United States Patent
Ollivier

(10) Patent No.: US 8,900,224 B2
(45) Date of Patent: Dec. 2, 2014

(54) KIT FOR PENETRATING THE CARDIAC SEPTUM AND FOR IMPLANTATION OF A TRANSEPTAL LEAD, INCLUDING A LEAD FOR DETECTION/STIMULATION OF A LEFT HEART CAVITY

(75) Inventor: Jean-Francois Ollivier, Villiers-le-Bacle (FR)

(73) Assignee: Sorin CRM SAS, Clamart (FR)

( * ) Notice: Subject to any disclaimer, the term of this patent is extended or adjusted under 35 U.S.C. 154(b) by 1008 days.

(21) Appl. No.: 12/957,293

(22) Filed: Nov. 30, 2010

(65) Prior Publication Data

US 2011/0130752 A1  Jun. 2, 2011

(30) Foreign Application Priority Data

Nov. 30, 2009  (FR) ...................................... 09 58504

(51) Int. Cl.
*A61B 18/18* (2006.01)
*A61B 18/14* (2006.01)
*A61B 18/00* (2006.01)
*A61B 18/12* (2006.01)
*A61N 1/05* (2006.01)

(52) U.S. Cl.
CPC ... *A61B 18/1492* (2013.01); *A61B 2018/00273* (2013.01); *A61B 2018/00351* (2013.01); *A61B 18/1206* (2013.01); *A61B 2018/1435* (2013.01); *A61N 1/0573* (2013.01)
USPC .............................. 606/33; 606/129; 606/41

(58) Field of Classification Search
USPC .................................................... 606/32–52
See application file for complete search history.

(56) References Cited

U.S. PATENT DOCUMENTS

| 5,447,534 | A |   | 9/1995  | Jammet            |        |
|-----------|---|---|---------|-------------------|--------|
| 5,807,395 | A | * | 9/1998  | Mulier et al.     | 606/41 |
| 5,876,398 | A | * | 3/1999  | Mulier et al.     | 606/41 |
| 5,984,917 | A | * | 11/1999 | Fleischman et al. | 606/32 |

(Continued)

FOREIGN PATENT DOCUMENTS

| EP | 0 591 053 | 4/1994 |
| EP | 1 516 644 | 3/2005 |

OTHER PUBLICATIONS

Foreign Search Report (Annexe Au Rapport De Recherche Preliminaire Relatif a La Demande De Brevet Francais No. FR0958504 FA729183), Jul. 21, 2010.

*Primary Examiner* — Linda Dvorak
*Assistant Examiner* — Amanda Scott
(74) *Attorney, Agent, or Firm* — Foley & Lardner LLP

(57) ABSTRACT

A kit for penetrating the cardiac septum and for implanting a transeptal lead, including a lead for the detection/stimulation of a left heart cavity. This kit includes a screw lead (16) and a radio-frequency puncture generator (32). The lead includes: a lead body with a deformable sheath (18); a proximal end having an electrical connector (20) for coupling to an implanted medical device housing; a distal end having a lead head (22) with an electrode including a projecting conductive helical screw (24) for penetrating into the septum (10) due to a screw movement applied from the proximal end of the lead, and a conductor (26) connecting the electrode to the electrical connector, the electrode including the screw. The radio-frequency puncture generator (32) is connected to the electrical connector to provide a controlled application by the helical screw of a radio-frequency energy on the septal wall and, in conjunction with the screw motion applied to the lead head, punctures through and results in the lead head crossing through the septum wall.

7 Claims, 1 Drawing Sheet

(56) References Cited

U.S. PATENT DOCUMENTS

| | | | |
|---|---|---|---|
| 6,016,809 A | 1/2000 | Mulier et al. | |
| 6,086,582 A | 7/2000 | Altman et al. | |
| 6,443,950 B1 * | 9/2002 | Sutton | 606/41 |
| 6,565,562 B1 | 5/2003 | Shah et al. | |
| 6,704,605 B2 * | 3/2004 | Soltis et al. | 607/127 |
| 7,620,457 B2 | 11/2009 | Ollivier et al. | |
| 8,313,482 B2 * | 11/2012 | McIntyre et al. | 606/32 |
| 2002/0188340 A1 | 12/2002 | Bischoff | |
| 2005/0234444 A1 | 10/2005 | Hooven | |
| 2007/0021745 A1 * | 1/2007 | McIntyre et al. | 606/41 |

\* cited by examiner

KIT FOR PENETRATING THE CARDIAC SEPTUM AND FOR IMPLANTATION OF A TRANSEPTAL LEAD, INCLUDING A LEAD FOR DETECTION/STIMULATION OF A LEFT HEART CAVITY The present application claims the benefit of French Application No. 09-58504 entitled "Kit for penetrating the cardiac septum and for implantation of a transeptal lead, including a lead for detection/stimulation of a left cavity of the heart" and filed Nov. 30, 2009, which is hereby incorporated by reference in its entirety.

FIELD

The present invention relates to a kit for penetrating the cardiac septum to implant a transeptal lead, and more particularly for implanting a lead for detection/stimulation of a left heart cavity to continuously monitor the heart rhythm and deliver, if necessary, at the heart, electrical pulses for stimulation and/or resynchronization in response to a detected rhythm disorder.

It should be understood, however, that the present invention is not limited to the implantation of such leads for detection/stimulation, and it also applies to the implantation of a defibrillation lead and, even more generally, to any invasive surgical procedure requiring the passage of the cardiac septum, for example, to carry out clinical investigations in one or other of the left heart cavities. Further, the present invention also is applicable to angioplasty procedures, including mitral valve repair operations.

BACKGROUND

It is known that stimulation of the right heart cavities may be achieved by the implantation of an endocardial lead that is passed through the right peripheral venous network. However, to stimulate the left heart cavities, the situation is more complex. One solution often adopted is to introduce a lead into the right atrium and then pass it into the coronary system via the coronary sinus ostium. However, this implantation technique is not always feasible, especially when the conformation of the coronary sinus is too rough, or there is thrombosis.

Another solution, called the "transeptal approach" is to pass the lead through the interventricular or interatrial septum, or "cardiac septum", to stimulate the left heart atrial or ventricular cavity, depending on the configuration and placement of the lead. This procedure, as currently implemented, however, presents high operative risks, including, for example, accidental perforation of the aorta or dissection of the right atrium wall by a sudden, unintentional rotational movement of the needle. In any case, this technique is very difficult to implement and requires great skill by the surgeon who must be able to cross the septum and ensure a perfect positioning of the lead on the wall. Crossing of the septum is typically not to undertaken if there remains any doubt about the position of the needle.

The EP 1 516 644 A1 and its counterpart U.S. Pat. No. 7,620,457 describe a kit for penetrating the cardiac septum and for the placement of a trans-septal device that avoids the foregoing problems. The proposed technique is to implement a penetrating guide comprising a lead that is equipped at its distal end with a helical screw and a catheter guide having an internal lumen. The screw is oriented to be screwed into the wall of the septum in the location of the selected perforation site. Once the screw is anchored in place, the physician introduces a penetrating stylet into the internal lumen. The stylet is progressively driven into the guide catheter to puncture the septum, while being guided by the lead head anchored in place by the helical screw. This is said to secure the progression of the penetrating stylet. Once the septal wall is crossed, the guide catheter is pushed by the physician to penetrate into the hole just initiated by the penetrating stylet until it emerges into the left cavity. The operation continues with the removal of the penetrating stylet out of the guide catheter, followed by the extraction of the penetrating guide (by unscrewing the screw and withdrawing the penetrating guide). This leaves only the guide catheter in place, on which a dilator is threaded to enlarge the hole. A main catheter is then put in place to ensure communication with the left heart cavity, and to allow the introduction and positioning of the detection/stimulation lead relative to the endocardial stimulation site selected by the practitioner in the left heart cavity (usually the atrium).

This technique allows a perfectly safe puncture of the septal wall. However, it also involves a large number of different components that must be manipulated (e.g., a guiding lead, a penetrating stylet, a temporary guide catheter, a dilator, a final guide catheter, a detection/stimulation lead). Moreover, if the manipulation technique follows the normal operating procedures of a trained practitioner, it remains relatively difficult and slow to execute.

It is known to employ mechanical units for cutting or penetrating tissue, such as chisel, or a traditional detection/stimulation lead that has a retractable screw lead, which is generally considered the most appropriate system for fixing the lead in the left heart cavity wall after crossing the septum. However, leaving a cutting element, even if in a retracted position, on a permanently implanted lead in the left ventricle is a concept difficult for some practitioners to accept. An alternative to using a cutting tool integrated in a permanent lead is to use a cutting tool that could be used and then removed. However, such a design would create a number of additional challenges, particularly in terms of safety of use.

OBJECT AND SUMMARY

It is, therefore, an object of the present invention to provide a kit for penetrating the cardiac septum that will maintain at least the same safety level as the prior art techniques, while reducing the number of components needed for its implementation.

Another object of the present invention is provide a kit for penetrating the cardiac septum and for implanting a transeptal device, which combines a simplicity of implementation and a safety of penetration, once the site of intervention is selected, while minimizing the invasiveness of the intervention.

Another object of the present invention is to provide a kit for penetrating that can be implemented by operational techniques comparable to prior art techniques already known to and used by practitioners (for example, an implantation of a screw lead through the subclavian access), that can be easily adapted to a penetration of the septum.

Broadly, the present invention combines a screw pacing lead with a cutting tool that applies locally a low power radio-frequency (RF) energy, to create a very small opening in the cardiac tissue, particularly in the septal wall, which is called an "RF puncture." A suitable RF electronic generator is used to create the low power RF energy. In one embodiment, an RF puncture is made by applying RF energy of low power (e.g., 5-25 W), for a short period of time (e.g., 1-3 s) under high voltage (e.g., 150-180 V), so as to cause minimal collateral damage to surrounding tissues.

It should be understood that the technique of "RF puncture" is distinct from the technique of "RF ablation." RF ablation concerns applying RF energy at a higher power (e.g., 35-50 W) for an extended time (e.g., 60-90 seconds) at a lower voltage (e.g., 35-50 V). In the context of the application considered for the present invention, an RF ablation would create a larger lesion than an RF puncture, with thermal destruction of surrounding tissues.

U.S. Pat. No. 6,086,582 describes a device for locally treating ischemic sites or arrhythmia generator sites of a cardiac cavity, by in situ delivering drug doses. The drug delivery is performed using a screw lead that the practitioner anchors in the selected site to be treated. In addition, if desired, damaged tissues may be ablated by locally injecting through the anchoring screw RF energy at high power. This energy will destroy the tissues (ablation) in the area located around the screw. However, this prior art ablation technique would not be suitable to perform a puncture which is a very accurate and clean penetration of the cardiac wall and, a fortiori, of the septal wall. Rather, the difficulty of controlling the destruction of the tissues around the screw as discussed in U.S. Pat. No. 6,086,582 would create an unacceptable operating risk in the context of penetrating the septum.

According to one embodiment, the present invention is thus directed to a dedicated kit for penetrating the cardiac septum and for implanting a transeptal lead, which provides the benefits of simplicity, safety and being minimally invasive. One such kit comprises, in combination, a screw type lead and a radio-frequency puncture generator.

One preferred screw type lead is of the kind described in U.S. Pat. No. 6,086,582, described above, and which includes: a lead body with a sheath of deformable material having a proximal end and a distal end and a conductor extending along the sheath. The proximal end has an electrical connector that can be coupled to an implanted medical device housing, and to an RF puncture generator (as discussed herein). The distal end has a lead head with an electrode including a projecting helical screw. The helical screw is at least partially conductive and able to penetrate the wall of the septum as a result of a screw motion of the lead head imparted at the proximal end of the lead (or, as the case may be, at the lead head by a stylet). The conductor extends along the sheath and connects the electrical connector to the electrode including the screw.

In operation, the RF puncture generator is connected to the electrical connector and operated to provide the desired controlled RF energy to the helical screw. This delivery of a controlled RF energy is concurrently with movement of the screw that is imparted to the lead head while the lead head crosses the septal wall.

According to an embodiment of the invention, the cardiac wall is a cardiac septum wall, the anchoring screw includes a distal part and a proximal part. The distal part is electrically isolated and has a traction function to pierce the tissue and as it rotates to draw the lead towards the tissue. The proximal part is electrically conductive and has a cutting function such that, as the distal end draws the proximal end toward the septal wall tissue, the RF energy is delivered and cuts the tissue locally at the proximal part of the screw. Thus, as the rotational movement of the screw continues, it punctures a passage for the lead to pass through the septum as the screw distal part continues to rotate and advance through the septum, pulling the proximal part along while cutting the tissue. Thus, the lead of the present invention ensures the penetration of the cardiac septum wall and then the crossing of the septum by the lead head to allow a transeptal implantation of the lead.

Preferably, the lead is a detection/stimulation lead for a left heart cavity, and the electrode of the lead head is a detection/stimulation electrode.

The anchoring screw may be either a screw extending axially from the lead head, or a movable screw that is retractable into a housing of the lead head.

According to one optional embodiment, the sheath of the lead body may have a torsional rigidity that is not sufficient to allow transmission over its entire length of a rotating movement from the proximal end of the lead, and the kit also includes a removable stylet that is introduced in a lumen of the lead body and movable in translation within that lumen to the lead. In such an embodiment, the stylet has a sufficient torsional rigidity to enable transmission over its entire length of a rotating movement from the proximal end of the stylet, for screwing the helical screw. A means of coupling the stylet in rotation with the lead head is provided in a conventional manner.

In yet another embodiment, the kit of the present invention also includes a penetrating guidewire that is to be connected at one end to the RF puncture generator, and thus to deliver at the other end a controlled RF energy. This guidewire can be used to pre-puncture the septum for verifying that the site selected for the puncture is acceptable prior to puncturing the septum. The lead in this embodiment is configured as a carrier lead that can be slipped over or threaded on the guidewire such that the penetrating guide wire connected to the RF puncture generator delivers the controlled radio-frequency energy at a penetration site of the septum where a pre-puncture is to be made. Then, the lead can be connected to the RF generator if the site is confirmed and a puncture is to be made there.

BRIEF DESCRIPTION OF THE DRAWINGS

Further features, characteristics, and advantages of the present invention will become apparent to a person of ordinary skill in the art from the following detailed description of embodiments of the present invention, made with reference to the annexed drawings, in which like reference characters refer to like elements, and in which.

DETAILED DESCRIPTION

Figure 1:
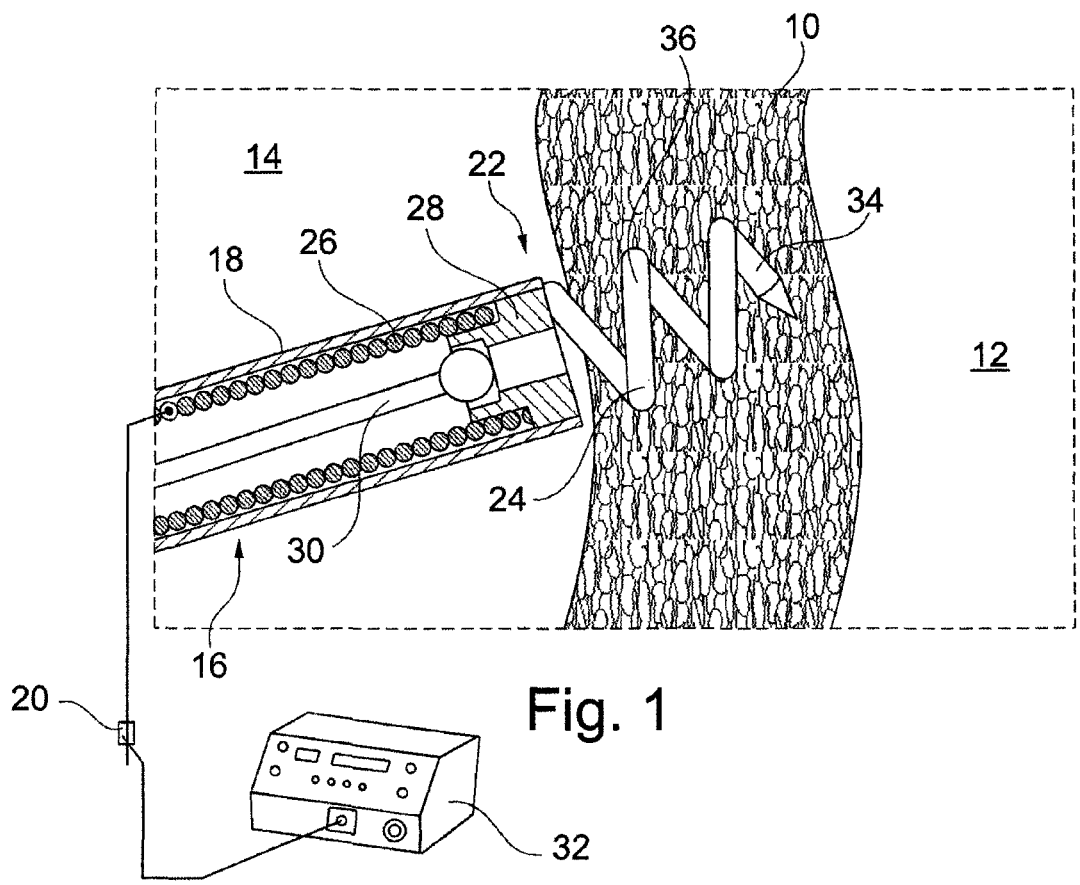
FIG. 1 is an illustration in partial cross section of a first embodiment of a penetrating kit of the present invention, in a configuration corresponding to the beginning of the penetration operation of the septum.
Figure 2:
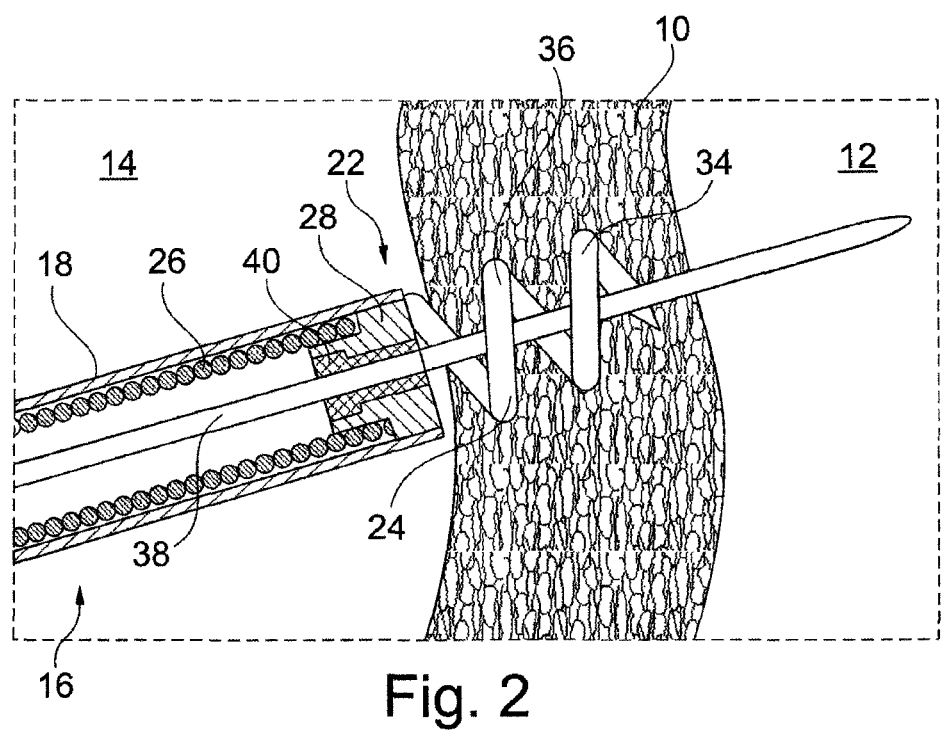
FIG. 2 is an illustration in partial cross section of a second embodiment of a penetrating kit of the present invention, in a configuration corresponding to the beginning of the penetration operation of the septum.

With reference to FIGS. 1 and 2, and the examples described below, the reference 10 designates the wall of the cardiac septum, e.g, the wall separating the left atrium cavity 12 from the right atrial cavity 14; the wall 10 thickness is approximately 2 mm. It should be understood, however, that the description can similarly be implemented to achieve the penetration of the part of the cardiac septum between the left ventricle and the right ventricle. Indeed, as will be understood by a person of ordinary skill in the art upon reading the description herein, the invention is easily applicable to penetrating relatively thicker walls, as in the case of the interventricular septum.

The kit of the present invention provides a puncture tool that is the detection/stimulation lead itself, this lead being a screw lead (e.g., either a fixed or retractable screw). More specifically, as shown FIGS. 1 and 2, a lead 16 includes a lead body having a conventional structure including a sheath 18 made of a deformable material, typically a silicone or polyurethane sheath.

The lead 16 is terminated at its proximal end by an electrical connector 20 (FIG. 1) for coupling the lead 16 to the housing of an implanted medical device (e.g., a pacemaker or a resynchronizer, not shown) after the lead is located and installed at the definitive selected stimulation site.

At its distal end, the lead 16 has a lead head 22 with a helical screw 24 comprising non-touching turns with a diameter of about 1 to 1.2 mm, and made partially or completely of a non-isolative conductive material. Screw 24 is electrically connected to an inner conductor 26 by means of a metal tip 28. The conductor 26 is, for example, a coiled conductor extending along the entire length of the sheath 18 to the electrical connector 20, thus providing electrical continuity between the helical screw 24 and connector 20.

The sheath 18 may be chosen to provide some torsional rigidity, so as to transmit torque from the proximal end of the lead (e.g., at the electrical connector 20) to the distal end of the lead head 22 to rotate the screw 24 for penetrating by screwing into the heart tissue. This axial rotation movement is applied, as appropriate, either directly to the lead body, or at the plug connector for a pin driven lead (in which the proximal connector assembly is secured to an axial conductor extending inside the lead body, this conductor itself being free in rotation and connected to the helical screw at its distal end). Such drive mechanisms are conventional and known to persons of ordinary skill in the art and therefore are not discussed in detail herein. In this regard, it should be understood that preferably, when a retractable screw is used (also through a mechanism known in the prior art), the rotating movement applied to the inner conductor simultaneously deploys the retracted screw out of its housing and into the myocardial wall to ensure its penetration.

Alternatively, or in addition, if the torsional rigidity of the lead body is not sufficient to drive the screw, it is possible to use a special screw stylet 30 inserted into an inner lumen of the lead to drive the screw. The distal end of this stylet is then coupled to the metal tip 28 to allow rotation of the latter, and thus of the screw 24, directly from the proximal end of the lead.

A lead screw, such as the lead 16 as described above, is generally used as a detection/stimulation lead after the screw is anchored at the desired endocardial stimulation site. This also is the case in the context of the present invention, although the endocardial pacing site is a site located in the left heart cavity 12, after crossing of the septum 10 by lead 16.

Broadly, the present invention uses such a detection/stimulation lead not only for its detection/stimulation function, a function that will still be ultimately achieved after crossing the septum, but also as a penetration tool for achieving the required puncture of the septum wall.

To this end, in a preferred embodiment, the lead 16 is connected at its proximal end during the penetration of the septum to an RF puncture generator 32 whose output terminal is coupled to the electrical connector 20. As noted, connector 20 can subsequently be disconnected from the RF puncture generator and connected, in accordance with its normal function, to a housing of an implantable medical device such as a pacemaker or resynchronizer.

It should be understood, however, that the connection of the RF puncture generator 32 to the connector 20 must be in a way will permit the doctor to use, if needed, a traditional stylet during the implantation puncture, to ensure that in addition to the torsion, a sufficient axial force is applied to keep the lead head on the punctured zone, in addition to the traction brought by the screw 24, so as to secure the screw into the wall for the penetration operation.

One suitable RF puncture generator 32 is a known model, such as the BMC Radio Frequency Perforation Generator, available from Baylis Medical Company, Inc.

The RF energy produced by the generator 32 is applied to the helical screw 24 via the electrical connector 20, the spiral conductor 26 and the metal tip 28. The RF energy will allow the cutting of the tissue in an area having a very small dimension that is defined by the helical screw (whose diameter is, as stated above, on the order of 1.0 to 1.2 mm). The lead body rotation will help to advance the screw 24 within the wall of the septum 10 as the puncture progresses.

Screw 24 preferably has a distal part 24 and a proximal part 36 which are contiguous sections of the helical coil. The distal part 34 of the screw is electrically isolated by a coating of parylene or of another material on the distal part 34 of the screw, for example, along an extent of a coil or a length on the order of 0.8 mm in an axial direction. The proximal part 36 is conductive and not insulated, and is thus the electrically active part of the screw 24 and preferably the only electronically active part. This allows for a local concentration of the flow of RF energy in the corresponding region, with the distal part 34 having only a mechanical traction function.

With this configuration, the isolated distal part 34 acts as a mechanical traction part to allow progression of the lead 14 into the septum, while the electrically active distal part 36 ensures the cutting of the tissue. This configuration is particularly suitable for thick walls such as the interventricular septum, thus avoiding any long-term risk due to the presence of the definitive lead body passing through the mitral valve.

With reference to FIG. 1, a procedure corresponding to inserting a lead of a first embodiment will now be described.

The first step is to locate the puncture site, by manipulating the lead tip 16 via a conventional stylet 30 inserted into the lead or by a guide catheter, the assembly being inserted into the cavity 14 of the right atrium until it presses against the septum wall 10 at a target penetration site.

Once this site is reached, the practitioner applies to the lead body, and consequently to the helical screw 24, a rotation movement through the sheath 18 and/or stylet 30 from the proximal end of the lead, e.g., at the electrical connector 20. This maneuver has the effect that the helical screw 24 penetrates the wall of the septum 10, and the completeness of the screwing being detected tactilely by the practitioner, because of the resistance to rotation.

The next step is to perform conventional electrical testing and radiographic examination according to different inclinations, to confirm the selected puncture site. If the position is not satisfactory, the practitioner can then unscrew the lead head and move it under control to another point, and test the new site.

Once a site is confirmed as acceptable, the electrical connector 20 is then connected to the RF puncture generator 32. The RF puncture generator is then activated to apply the RF energy to the screw 24, the current return being carried out by a ground electrode applied to the patient's body.

While continuing to activate the RF puncture generator, the practitioner maintains (through the sheath 18 and/or the stylet 30) the pressure of the lead head 22 against the wall of the septum 10, and applies to the lead body a controlled gradual rotation to advance the helical screw 24 in the wall 10 as the puncture progresses.

Once the wall has been completely traversed, the RF generator 32 is stopped and disconnected from the lead connector 20.

The next step is to push the lead 16 beyond the septum wall 10 through which a puncture has been made, from one side to the other side, until the helical screw 24 approaches the chosen endocardial stimulation site in the left heart cavity 12 (atrium or ventricle). There, the lead head will be permanently anchored in place by a further rotation motion imparted on the screw.

With reference to FIG. 2, a second embodiment of the invention, based on a technique called Over The Wire ("OTW") or "wire guidance" that uses a very thin guidewire 38 provided at its distal end with a very flexible atraumatic termination. In the context of the present invention, the guidewire 38 is a conductor that may be connected to the RF puncture generator 32. The body of the guidewire 38 is insulated, and it is active only in its distal end so as to apply locally the RF energy to achieve a pre-puncture of the septum on a very small diameter. An appropriate RF guidewire is, for example, the model Nykanen RF Wire, available from Baylis Medical Company, Inc. Corporation, which has at its end a reduced diameter of 0.016 inch (0.41 mm).

The lead 16 used with such a wire 38 is in this configuration called a "carrier" lead. It is provided with a sealing joint 40, in place of the metal tip 28, to interface with the guidewire 38.

In one preferred implementation of this second embodiment, the guidewire 38 is first introduced and lead 16 is slid along the guidewire 38 to the chosen site. The advantage of this implementation is the possibility of using the guidewire 38 to confirm that the site selected for the puncture is a suitable area: once the pre-puncture with RF guidewire is performed, then it is only necessary to just keep pushing the guidewire 38, which easily leads into the left cavity 12, if the pre-puncture is correct. Another advantage of this implementation is that it provides additional guidance of the lead 16 during the duration of the puncture operation (i.e., during the application of the RF energy to the screw 24). In other words, the guidewire 38 performs a pre-puncture for just the guidewire 38, and then the lead 16 is used as described above to perform the puncture for the lead 16.

A second form of implementation is to implant first the carrier lead 16 on the wall by screwing, but without puncture, and then insert the penetrating guidewire 38 in the carrier and operate the RF generator 32 to perform the pre-puncture by the guidewire 38. The guidewire passes then into the left atrium. The physician can then push the guidewire 38 in the left cavities (leaving the lead secured to the septum wall, and confirm by radiographic examination the puncture site. Once confirmed, then the RF generator 32 is connected to the carrier lead 16 (which is also the definitive lead) to perform the puncture of a larger diameter for the passage of lead 16, the carrier lead 16 thus being guided by the guidewire during the puncture, which is another advantage of this variant.

The present invention has particular advantages over prior art. One advantage is the accuracy of the punctured site, based upon the prior screwing of tip of the screw lead, which provides an accurate anchoring of the latter, avoiding any uncontrolled cutting that could lead to serious complications.

Another advantage is that the implantation procedures only use techniques similar to current practices, for example, following a traditional subclavian access and using efforts of rotation and axial pressure that are familiar to a trained practitioner.

Finally, a major advantage of RF puncture made by the technique of the present invention is that the effort to be applied is independent of the nature or thickness of tissue. This advantage is further enhanced by the helical shape of the screw, whose natural progression in tissue by transmission of a rotation torque can be very finely controlled, much better than the advance by successive pressures on a needle as in the prior known conventional RF puncture techniques.

One skilled in the art will appreciate that the present invention may be practiced by other than the embodiments described above, which are provided for purposes of illustration, and not of limitation.

The invention claimed is:

1. A kit for puncturing a wall of a cardiac septum, comprising:
    a screw lead including:
        a lead body having a sheath of a deformable material;
        a proximal end having an electrical connector;
        a distal end having a lead head including an electrode comprising a projecting helical screw, said projecting helical screw having a first conductive part and a second electrically isolated part, the second electrically isolated part having a traction function for penetrating the septum wall end in response to a screw motion applied to the lead head, the first conductive part having a septum wall cutting function for delivering a controlled radio-frequency energy to the septum wall concurrently with a screw motion applied to the lead head, said radio-frequency energy being controlled to puncture said septum wall whereby the lead passes through the punctured septum wall; and
        a conductor extending along the sheath, electrically connecting said electrical connector and the first conductive part of the projecting helical screw; and
    a radio-frequency puncture generator having a controlled radio-frequency energy for puncturing a septum wall and an output to connect to said lead electrical connector;
    wherein the screw lead is a detection/stimulation lead, and said electrode of the lead head comprises a detection/stimulation electrode.

2. The kit of claim 1 wherein the helical screw is further configured to anchor the lead such that the lead passing said septum wall is anchored to make a transeptal implantation of the lead.

3. The kit of claim 1, wherein the anchoring screw is a fixed screw axially extending from the lead head.

4. The kit of claim 1, wherein the lead head comprises a housing and wherein the anchoring screw comprises a moveable screw having a retracted position inside the housing and an extended position outside of the housing.

5. The kit of claim 1, wherein the anchoring screw second electrically isolated part is distal of and extends from said first conducting part.

6. The kit of claim 1, wherein the lead further comprises a lumen and a sheath, the sheath having an insufficient torsional rigidity to transmit over its entire length a rotating movement imparted at the proximal end of the lead, further comprising:
    a removable stylet, inserted into a lumen of the lead body and movable in translation within that lumen to the lead head;
    means for coupling said stylet in rotation with the lead head,
    said stylet having a sufficient torsional rigidity to transmit over its entire length a rotating movement imparted at the proximal end of the stylet, for rotating the helical screw.

7. The kit of claim 1, further comprising:
    a radio-frequency penetrating guidewire having a proximal end and a conductive distal end, wherein, in response to said distal end being positioned at a pre-puncture site of said septum wall and said proximal end being connected to said controlled radio-frequency energy output of said RF puncture generator, said conductive distal end delivers said controlled radio frequency energy to pre-puncture said the septum wall, and wherein the lead further comprises a carrier lead mounted on said guidewire.

* * * * *